United States Patent
Banik et al.

(10) Patent No.: US 11,278,681 B1
(45) Date of Patent: Mar. 22, 2022

(54) TAMPER EVIDENT ADAPTOR CLOSURE

(71) Applicants: Robert Banik, Hollywood, FL (US); Peter Lehel, Boca Raton, FL (US)

(72) Inventors: Robert Banik, Hollywood, FL (US); Peter Lehel, Boca Raton, FL (US)

( * ) Notice: Subject to any disclaimer, the term of this patent is extended or adjusted under 35 U.S.C. 154(b) by 359 days.

(21) Appl. No.: 16/281,925

(22) Filed: Feb. 21, 2019

Related U.S. Application Data (60) Provisional application No. 62/632,758, filed on Feb. 20, 2018.

(51) Int. Cl.
| | | |
|---|---|---|
| *A61M 5/50* | (2006.01) | |
| *A61M 5/31* | (2006.01) | |
| *A61M 39/20* | (2006.01) | |
| *A61M 39/10* | (2006.01) | |

(52) U.S. Cl.
CPC ........ *A61M 5/5086* (2013.01); *A61M 5/3134* (2013.01); *A61M 39/20* (2013.01); *A61M 2039/1077* (2013.01)

(58) Field of Classification Search
CPC ...... A61M 5/5086; A61M 5/50; A61M 5/504; A61M 39/20; A61M 2039/1077; A61M 2039/1094
See application file for complete search history.

(56) References Cited

U.S. PATENT DOCUMENTS

| | | |
|---|---|---|
| 722,943 A | 3/1903 | Chappell |
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |

(Continued)

FOREIGN PATENT DOCUMENTS

| | | |
|---|---|---|
| GB | 486367 | 6/1938 |
| WO | WO2008/000279 | 1/2008 |
| WO | WO 2017086607 | 5/2015 |

*Primary Examiner* — Nathan R Price
*Assistant Examiner* — Tasnim Mehjabin Ahmed
(74) *Attorney, Agent, or Firm* — Malloy and Malloy PL; Jennie S. Malloy (57) ABSTRACT

A closure structured to adapt a syringe for connection to an incompatible standardized medical connector, including either a male or female ISO 80369 series ENFit® connector. An adapter body has an inlet port and an outlet port disposed in fluid communication with one another. The inlet port is dimensioned and configured to accommodate attachment to a discharge port of the syringe and the outlet port is dimensioned and configured to accommodate attachment to the standardized connector. A tip cap is removably connected to the adapter body in flow sealing relation to the outlet port. The closure may include a tamper evident assembly including a sleeve removably disposed in enclosing relation to the adapter body and tip cap and a retainer structure is disposed in removably retaining relation to the sleeve.

10 Claims, 5 Drawing Sheets

(56) References Cited

U.S. PATENT DOCUMENTS

| | | |
|---|---|---|
| 3,323,798 A | 6/1967 | Miller |
| 3,364,890 A | 1/1968 | Andersen |
| 3,368,673 A | 2/1968 | Johnson |
| 3,574,306 A | 4/1971 | Alden |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 7/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A * | 10/1976 | Fuson .................. A61M 39/20 |
| | | 220/287 |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| 5,057,093 A | 10/1991 | Clegg et al. |
| D323,392 S | 1/1992 | Byrne |
| 5,085,332 A | 2/1992 | Gettig et al. |
| 5,090,564 A | 2/1992 | Chimienti |
| 5,135,496 A | 8/1992 | Vetter et al. |
| 5,163,922 A | 11/1992 | McElveen, Jr. et al. |
| 5,165,560 A | 11/1992 | Enniss, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 * | 3/2001 | Jansen ................ A61M 5/3134 |
| | | 604/111 |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |

(56) References Cited

U.S. PATENT DOCUMENTS

| | | |
|---|---|---|
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 * | 11/2017 | Vitello .................. A61M 39/20 |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,758,684 B1 | 9/2020 | Vitello et al. |
| 10,773,067 B2 | 9/2020 | Davis et al. |
| 10,888,672 B1 | 1/2021 | Vitello |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 * | 3/2021 | Hunt ................... A61M 5/5086 |
| 11,040,149 B1 | 6/2021 | Banik |
| 11,040,154 B1 | 6/2021 | Vitello et al. |
| 11,097,071 B1 | 8/2021 | Hunt et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0046962 A1 | 4/2002 | Vallans et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |

(56) References Cited

U.S. PATENT DOCUMENTS

| | | |
|---|---|---|
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin |
| 2014/0353196 A1 | 12/2014 | Key |
| 2015/0182686 A1 | 7/2015 | Okihara |
| 2015/0191633 A1 | 7/2015 | De Boer et al. |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0250420 A1 | 9/2016 | Maritan et al. |
| 2016/0279032 A1* | 9/2016 | Davis .................... A61M 5/142 |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0078684 A1 | 3/2018 | Peng et al. |
| 2018/0089593 A1 | 3/2018 | Patel et al. |
| 2018/0098915 A1 | 4/2018 | Rajagopal et al. |

* cited by examiner

TAMPER EVIDENT ADAPTOR CLOSURE

CLAIM OF PRIORITY

The present application is based on and a claim of priority is made under 35 U.S.C. Section 119(e) to a provisional patent application that is currently in the U.S. Patent and Trademark Office, namely, that having Ser. No. 62/632,758 and a filing date of Feb. 20, 2018, which is incorporated herein by reference in its entirety.

BACKGROUND OF THE INVENTION

Field of the Invention

This invention is directed to a closure structured to adapt a syringe for connection to an incompatible standardized medical connector, including a female or male ISO 80369 series ENFit® connector, which is a patient safety initiative, designed to ensure that feeding tube connectors are incompatible with connectors for unrelated delivery systems and which may also include tamper evident capabilities.

Description of the Related Art

Medical patients, when being treated at a healthcare facility commonly receive a drug, other prescribed medication and/or other liquids in a variety of ways, but specifically including intravenous tubes, catheters, etc. By way of example, a patient may be connected via a catheter, or a variety of other tubes, etc. to one or more delivery systems for purposes of receiving a prescribed medicine, oxygen, enteral nutrition, anesthesia, etc.

The connectors operatively associated with such different delivery systems are often compatible and can be connected to each other. However, in some cases a medicine, food composition, air, gas and/or other fluids have been accidentally delivered to a patient when a syringe or other device is wrongfully interconnected to a delivery tube. Such errors, which can cause serious injury and even death, are commonly referred to in the medical profession as "tubing misconnections".

To avoid such "misconnections" there have been attempts to standardize medical connectors, based on their category of utilization, in order to eliminate the potential for two unrelated delivery systems to be attached together. By way of example, utilizing a standardized connector which is not compatible for attachment to a Luer type of connector, including slip fittings or other conventional connectors, an enteral syringe (e.g., containing a food composition intended to be taken orally), could not be connected to an IV catheter to permit entry into the blood stream intravenously, thereby avoiding potentially serious injury to patients.

The International Organization for Standardization (ISO) has taken steps to mitigate the likelihood of "tubing misconnections" through the creation of an ISO 80369 series of connectors. This has resulted in the promotion of patient safety by specifying international standardized designs of connectors for different healthcare application categories. Such healthcare application categories include respiratory, enteral, urology, limb cuff inflation, neuraxial and intravenous (IV). Further, in order to get the technical and market expertise, the ISO has encouraged industry to be part of working groups to develop safe systems, without introducing any other safety concerns.

Part 3 of the ISO series (80369-3) is dedicated to enteral application. Accordingly, a standardized ISO enteral connector design has been developed and is known in the medical and related industries as the ISO series 80369-3 ENFit® connector. ENFit® is a registered trademark of the Global Enteral Device Supplier Association (GEDSA). The GEDSA is a nonprofit trade association formed to help introduce international standards for healthcare tubing connectors. It is comprised of manufacturers, distributors and suppliers of enteral nutrition devices worldwide and facilitates information flow, which is intended to increase patient safety and optimal delivery of enteral feeding, by reducing the risk of "tubing misconnections." Accordingly, the ENFit® connector is not compatible with a Luer type of connector or other conventional connectors, thereby eliminating or significantly reducing the possibility of misconnection between enteral feeding administration sets and incompatible delivery devices.

However, since the relatively recent introduction of the ENFit® connector design, many healthcare facilities still maintain a relatively large inventory of enteral syringes and/or oral syringes which, as indicated, are purposely incompatible with the ENFit® connector. As a result, there is a need in the medical field and medical component supply industry for an adapter which facilitates the connection of an enteral and/or oral syringe to an ENFit® connector, associated with a delivery system. The conversion of conventional syringes of this type to be compatible with the latest standardized connector allows a healthcare facility such as, but not limited to, hospitals and pharmacies to effectively reduce existing inventories in a cost-effective manner.

If any such adapter structure were developed, it would preferably have additional capabilities which enhance the versatility of its use. By way of example, it would be helpful if any such proposed adapter structure were to have tamper evident capabilities to provide clear evidence of an attempt to access or use the contents of an associated syringe. In addition, if any such proposed adapter structured were developed, it would preferably also include a closure which establishes a fluid sealing connection to an outlet port associated with the adapter structure, so as to regulate access to the contents of a conventional enteral and or oral syringe as well as selectively determine the dispensing thereof. In addition, it would be preferable for any such adapter structure to be capable of only a single use, due at least in part to the tamper evident structural capabilities associated therewith.

SUMMARY OF THE INVENTION

The present invention is directed to a closure structured to adapt a conventional syringe for connection to a standardized medical connector that would normally not be compatible for connection to the syringe. In more specific terms, the present invention is directed to various embodiments of a closure which may be attached to a conventional enteral syringe and/or oral syringe, and to also accommodate attachment of such a conventional syringe to an ISO 80369-3 series ENFit® connector.

As described herein, there has been a substantially universal conversion of the enteral syringe and enteral accessory market to the ISO standardized ENFit® connection, in order to enhance patient safety and prevent or significantly restrict the possibility of "tubing misconnections" between syringes or other delivery devices and incompatible enteral type delivery systems. However, numerous medical care facilities are thought to still maintain a substantial inventory of the conventional enteral and/or oral syringes. By providing an adaptive closure structure, the present invention offers a cost-effective way to eliminate the existing inventories of enteral or oral syringes, which are incompatible with the ENFit® connector provided.

Accordingly, in at least one embodiment, the adaptor closure of the present invention comprises an adapter body having an inlet port as well as an outlet port disposed in fluid communication with one another. In order to provide an effectively adaptive connection, the inlet port is structurally adapted to accommodate a fluid communicating connection with the discharge port, nozzle, etc. of the conventional syringe. In cooperation therewith, the outlet port is structurally adapted to accommodate a fluid communicating connection with the normally incompatible standardized connector, specifically including either a female or a male ENFit® connector.

In addition, an additional closure in the form of a tip cap may be removably connected to the adapter body in flow sealing relation to the outlet port thereof. As a result, the leakage, inadvertent escape or removal of the contents of the conventional enteral or oral syringe will be prevented. Further, the tip cap may be at least partially dimensioned and/or configured to correspond to the incompatible standardized connector to facilitate the establishment of a fluid sealing engagement with the outlet port. Further by way of example, at least a portion of the tip cap may be structured to assume either a female or male configuration. This facilitates the establishment of a fluid sealing connection with a female or male adapter body, which in turn, is structured to define a compatible connection with either a male or female ENFit® connector.

As will be explained in greater detail hereinafter, the additional closure in the form of a tip cap, having either the female or male configuration, may be selectively removed and reattached to the adapter body, in order to provide access and delivery of the contents of the enteral or oral syringe, to which the adapter body is attached.

Additional structural and operative features of the adaptor closure of the present invention include, in one or more embodiments, tamper evident capabilities. As such, the adaptor closure may include a tamper evident assembly comprising a sleeve and a retainer structure. The sleeve is operatively disposed in removable, enclosing relation over the adapter body and the tip cap. Removable disposition of the sleeve from its enclosing position relative to the adapter body and tip cap is accomplished, at least in part, by a retainer structure. In one or more embodiments of the adaptor closure, the retainer structure may be removably connected on the interior of the sleeve in retaining relation thereto.

More specifically, the adaptor closure of the present invention comprises in one or more embodiments a retainer structure that is removably connected to the exterior of the tip cap or the adapter body, such as by a frangible connection or attachment. Moreover, the retainer structure extends outwardly from the exterior of the tip cap and/or adapter body into at least partially interruptive relation to interior surface portions of the sleeve. Such interruptive positioning will restrict removal of the sleeve from its surrounding relation to the adapter body and tip cap. However, the frangible nature of the aforementioned connection or attachment enables the selective removal of the sleeve, when access and delivery of the contents of the syringe is contemplated.

Removal of the enclosing sleeve from the adapter body may be accomplished by exerting a pulling force on the sleeve, once the closure is attached to the conventional syringe, via its connection to the adapter body. Such a pulling force will result in a breakage of the frangible connection and a disconnection of the retainer member from an exterior of the tip cap or adapter body. As a result, both the retainer structure and the sleeve will be absent from the adapter body when access to the contents of the conventional syringe is attempted. Moreover, due at least in part to the breakage of the frangible connection and the detachment of the retainer structure, the sleeve will not be able to be replaced in its enclosing relation to the adapter body and tip cap. The absence of the sleeve from the adapter body and tip cap will be evidence of authorized use and/or tampering.

Additional features of the adaptor closure of the present invention include, in one or more embodiments, the provision of a movement restrictor connected to the adapter body in movement restricting engagement with the connected conventional syringe. The movement restrictor may be fixedly connected to the adapter body, preferably on the interior thereof, and disposed to engage and fixedly interconnect a discharge port of the conventional syringe to the adapter body. The structural features of the movement restrictor may thereby restrict or prevent rotation and removal of the discharge port and syringe relative to the adapter body.

In cooperation therewith, the tip cap may be connected to the adapter body by a threaded or other appropriate rotational connection. Therefore, the fixed attachment of the syringe to the adapter body will allow a threaded attachment and detachment of the tip cap into and out of its fluid sealing engagement with the outlet port of the adapter body. Once the sleeve has been removed from the adapter body and delivery of the contents of the conventional syringe is contemplated, the tip cap can be removed (unthreaded) by rotation from the adapter body. Thereafter, the tip cap can be rotationally reattached (threaded) on to the adapter body to re-establish its sealing engagement with the outlet port.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

DETAILED DESCRIPTION OF THE PREFERRED EMBODIMENT

Like reference numerals refer to like parts throughout the several views of the drawings.

Figure 1:
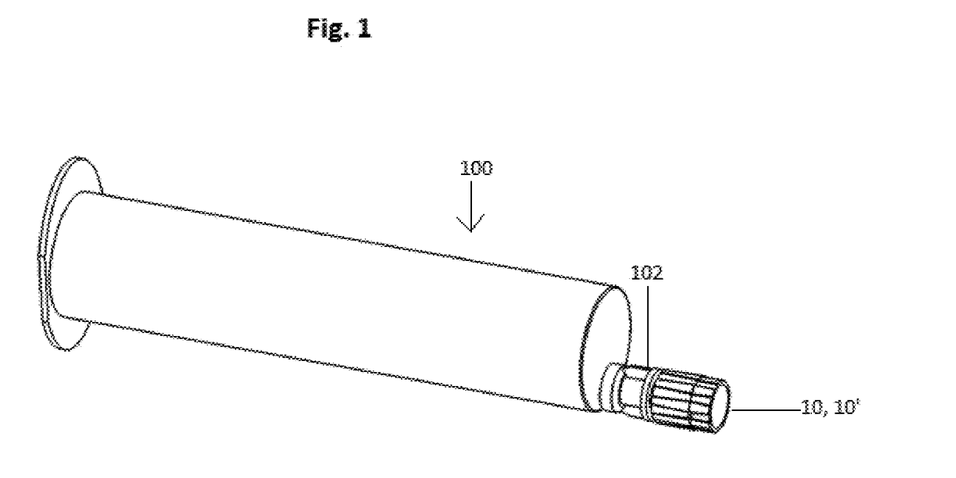
FIG. 1 is a perspective view of an adaptor closure according to at least one embodiment of the present invention, which is shown as being attached to a conventional syringe.
Figure 2:
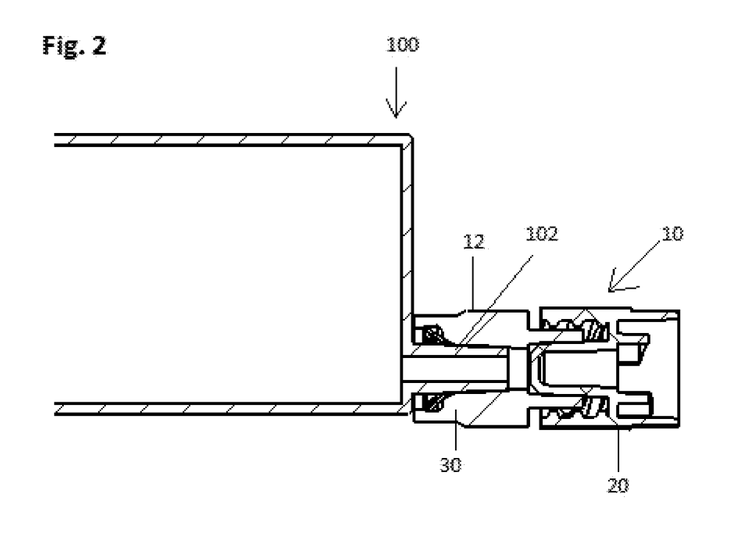
FIG. 2 is an interior sectional view in partial cutaway of the adaptor closure represented in FIG. 2, being partially assembled and also, attached to a syringe.
Figure 3:
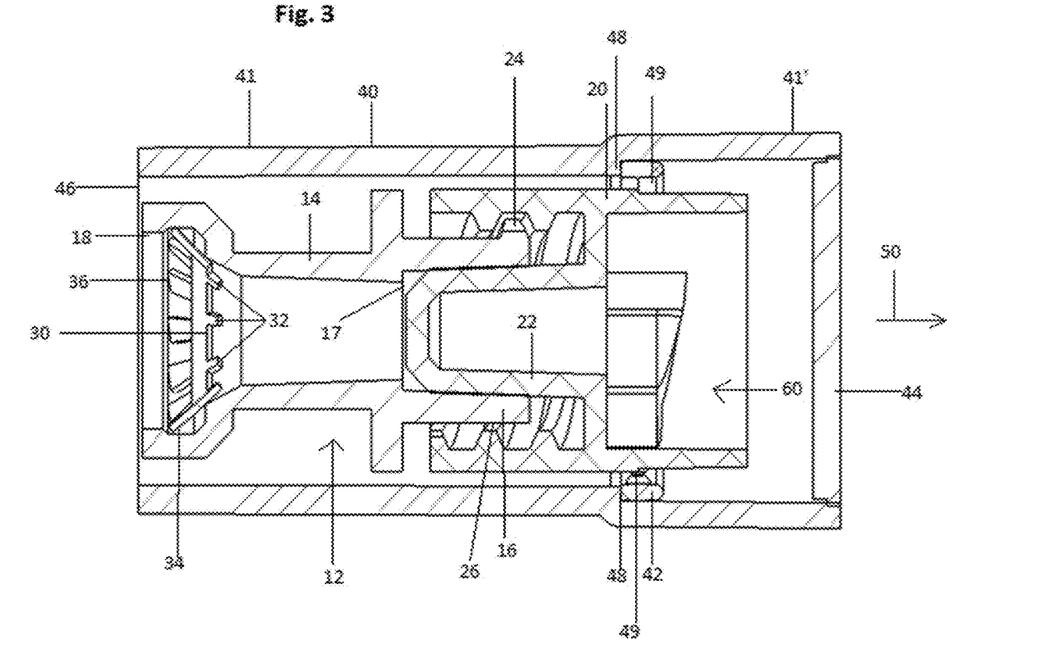
FIG. 3 is an interior sectional view in detail of the adaptor closure represented in FIG. 1, but illustrated as not being attached to a syringe and further, as including a tamper evident assembly.
Figure 4:
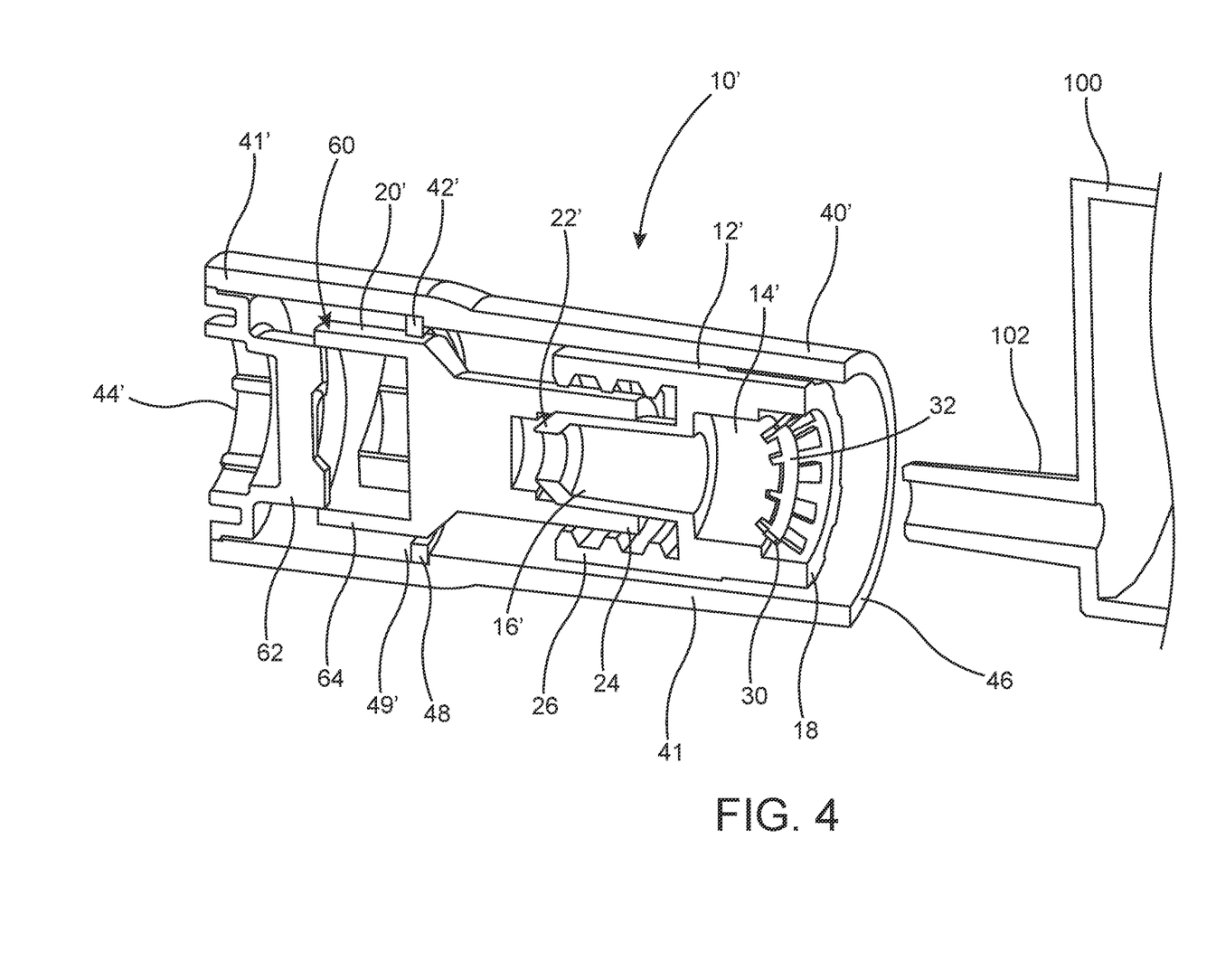
FIG. 4 is an interior sectional view in perspective and partial cutaway of an adaptor closure of the present invention in another embodiment, shown as not being attached to a syringe.
Figure 5:
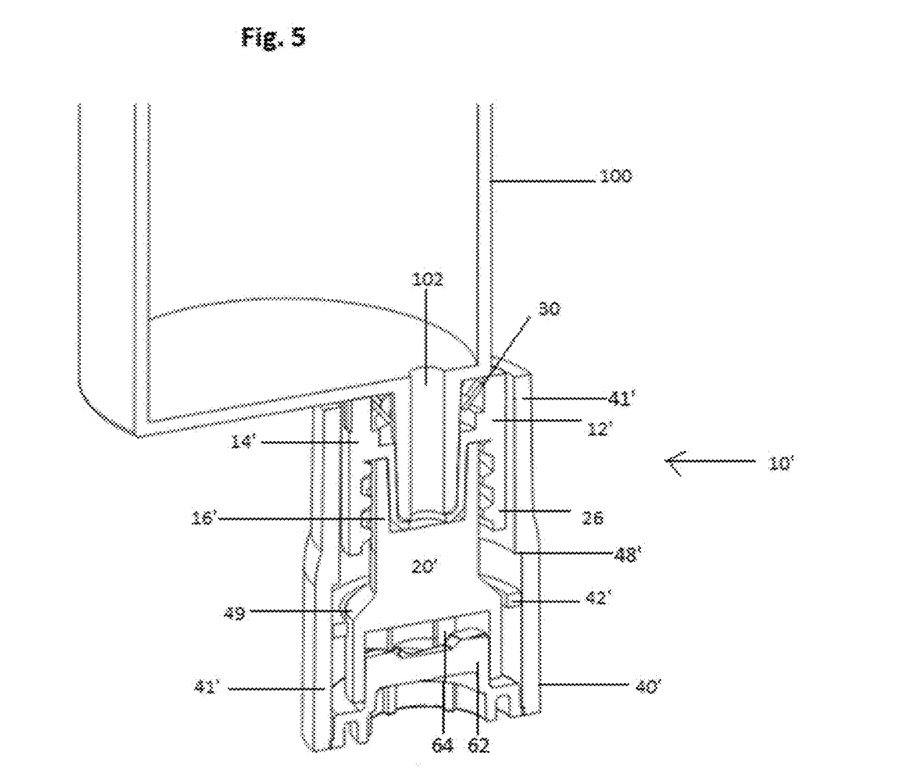
FIG. 5 is a detailed interior sectional view of the adaptor closure illustrated in FIG. 4 and showing it in an assembled state and as being attached to a syringe.
Figure 6:
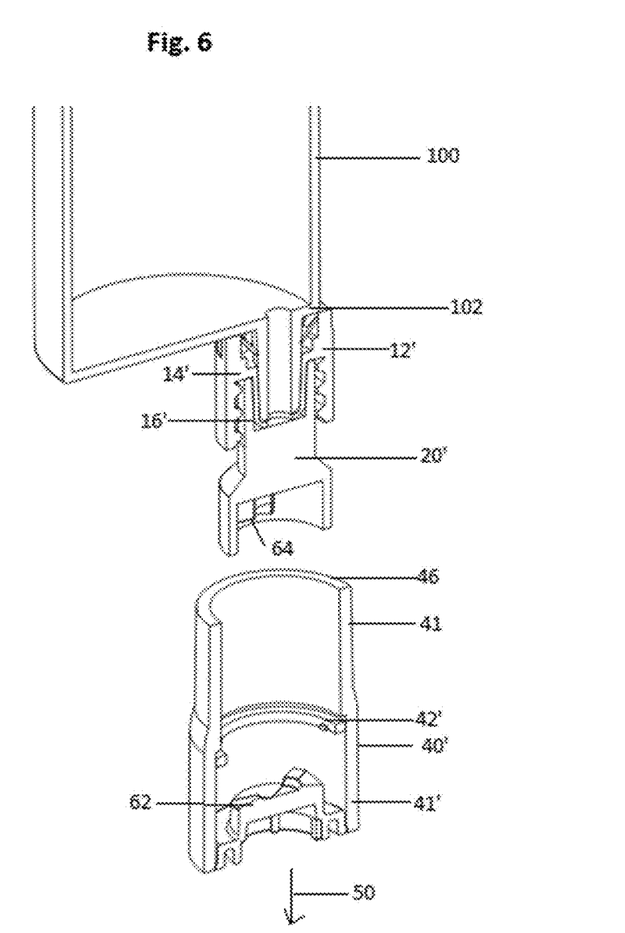
FIG. 6 is an interior sectional view of the adaptor closure illustrated in FIG. 5 in partial cutaway and exploded form.

As represented in the accompanying Figures, the present invention is directed to a closure 10, 10' structured to adapt a conventional syringe 100, such as an enteral syringe or oral syringe, for connection to standardized medical connector that it is not normally compatible with, such as and specifically including an ISO series 80369-3 ENFit® connector (not shown). Further, and as represented in FIGS. 2 and 3, the adaptor closure 10 may comprise a female configuration that is structurally adapted to facilitate connection of the conventional syringe 100 to a male standardized connector. In addition, and as represented in FIGS. 4-6, the adaptor closure 10' may comprise a male configuration, being structured to facilitate connection of the conventional syringe 100 to a female standardized connector.

With primary reference to FIGS. 2 and 3, the adaptor closure 10 includes an adapter body 12 including an inlet segment or inlet port 14 and an outlet segment or outlet port 16. The inlet port 14 and outlet port 16 are disposed in fluid communication with one another by virtue of an interconnecting opening 17. The adapter body 12 also includes an access opening 18 through which a discharge port 102 of the syringe 100 passes into a fluid sealing engagement with the inlet port 14. As such, the inlet port 14 shown in FIGS. 2 and 3 has a substantially female configuration that is cooperatively dimensioned and configured to the male configuration of the discharge port 102 in order to establish the aforementioned fluid sealing connection therebetween.

As set forth above, the adaptor closure 10 is structured to facilitate connection of the syringe 100 and discharge port 102 to a male standardized connector, including a male ENFit® connector. Accordingly, the outlet port 16 of the adapter body 12 has a female configuration cooperatively dimensioned and configured to a male configured portion of the standardized connector to establish a fluid sealing engagement therewith.

Additional structural features of the closure 10 include a tip cap 20 being structured to establish a fluid sealing engagement with the outlet segment or outlet port 16 of the adapter body 12. More specifically, and as perhaps best shown in FIG. 3, the tip cap 20 includes a flow restrictor 22 having a male structural configuration cooperatively dimensioned with the female outlet segment or port 16 so as to be disposed in fluid sealing engagement therewith. As also represented, the adapter body 12 includes one or more outwardly extending ribs or "threads" 24 cooperatively structured to establish a rotational, threaded engagement with internal thread structure 26, formed on the tip cap 20. This rotational threaded engagement of the tip cap 20 with the outlet segment or outlet port 16 of the adapter body 12 facilitates the disposition of the male flow restrictor 22 of the tip cap 20 into the aforementioned fluid sealing engagement on the interior of the outlet segment or outlet port 16.

Additional structural features of the closure 10 further facilitate both the rotational, threaded attachment and detachment of the tip cap 20 to or from the adapter body 12 and corresponding inlet segment or port 16. More specifically, the closure 10 can include a movement restrictor 30 that is preferably disposed within the adapter body 12 adjacent the inlet port or segment 14 and access opening 18. The movement restrictor 30 may include a flexible material construction and have an annular configuration, including a substantially open central interior. In addition, the movement restrictor comprises a plurality of outwardly protruding, spaced apart teeth 32 as shown in FIG. 3. One end of the adapter body 12 associated with the access opening 18, includes an interior surface recess 34 disposed, dimensioned and configured to fixedly retain the movement restrictor 30 therein. Due to the fact that the movement restrictor 30 is formed of a flexible material, it may be at least minimally collapsed and forced through the access opening 18. Once in substantial alignment with the interior surface recess 34, the inherent flexibility of the movement restrictor 30 allows it to expand such that the outer periphery thereof, as at 36, will engage within and be retained by the interior surface recess 34. As such, the movement restrictor 30 is fixedly locked in the adaptor body 12, in the intended operative position, by a "snap-fit" connection.

As should be apparent from a review of the Figures, the discharge port 102 the syringe 100 is connected to the closure 10 by a "push-on" force. Such a "push-on" force will serve to direct the discharge port 102 through the access opening 18 and through the open center of the movement restrictor 30 and into the interior of the inlet port 14. Once so positioned, the discharge port 102 of the syringe 100 will be fixedly connected to the adapter body 12 as represented in FIG. 2. As used herein, the "fixed connection" of the discharge port 102 is meant to describe the discharge port 102 as being substantially non-removable and substantially non-rotatable relative to the adapter body 12 and inlet segment or inlet port 14. Such a fixed connection is accomplished, at least in part, by the aforementioned flexible characteristics of the movement restrictor 30 in cooperation with the gripping engagement of the plurality of fingers 32 and interior surface portions of the movement restrictor 30 with the outer surface of the discharge port 102.

In order to establish and assure a fluid tight connection with the discharge port 104 and the inlet port 14, the tip cap 20 includes a one-way drive structure generally indicated at 60, which is shown in greater detail in the embodiment of FIG. 4. When the "push-on" force is exerted on the syringe 100, the adapter body 12 and the connected tip cap 20 will be forced inwardly towards the interior surface of the closed end 44 of the sleeve 40. Further, the one-way drive structure 60 is operable to at least temporarily lock the adapter body 12 and connected tip cap 20 into the interior of the sleeve 40, and prevent relative rotation therebetween. As a result, an external preferably clockwise twisting or turning of the syringe 100, when the discharge port 102 is within the inlet port 14, will cause a tightening therebetween, which in turn assures a fluid tight connection.

In the preferred embodiments, the discharge port 102 is sufficiently restricted against rotation relative to the adapter body, due to its engagement with the movement restrictor 30, to allow the tip cap 20 to be rotationally unthreaded and subsequently reattached, by a rotational threaded connection. However, the exertion of a tightening force on the syringe 100 and discharge port 102 can be accomplished.

Therefore, prevention of removal or rotation of the discharge port 102 relative to the adapter body 12 will allow a rotational, detachment (threaded) of the tip cap 20 from the outlet segment or port 16. Moreover, the fixed connection of the discharge port 102 relative to the adapter body 12 will also allow the tip cap 20 to be re-attached (threaded) in its sealing engagement with the outlet segment or port 16.

With further reference to FIG. 3, the adaptor closure 10 preferably also includes tamper evident capabilities defined, at least in part, by a tamper evident assembly including a sleeve 40 and a retainer structure 42. When operatively assembled, the sleeve 40 is disposed in surrounding, enclosing relation to both the adapter body 12 and the tip cap 20. The sleeve 40 includes a closed end 44 and an oppositely disposed open end 46. The open end 46 is disposed adjacent to or in substantial alignment with the access opening 18 of the adapter body 12. This alignment facilitates positioning of the discharge port 102 of the syringe 100 into the aforementioned fluid sealing connection with the inlet segment or port 14, through the access opening 18 and the movement restrictor 30.

As should also be apparent, the internal diameter or transverse dimension of the portion 41 of the sleeve 40 associated with the open end 46 is smaller than the diameter or transverse dimension of the portion 41" of the sleeve 40, which is associated with the closed end 44. As a result, at least the interior surface portion of the sleeve 40 includes a "stepped" configuration or structure 48. The stepped interior surface 48 may further define the junction of the smaller dimensioned portion 41 of the sleeve 40 with the larger dimensioned portion 41'.

In cooperation therewith, the aforementioned retainer structure 42 includes a diameter or transverse dimension which is larger than that of the sleeve portion 41 and more closely corresponds to that of the sleeve portion 41'. As such, the retaining member 42 is disposable in interruptive relation with the interior surface stepped portion 48 of the sleeve 40. Further, the retainer structure 42 is removably disposed on the exterior of both the adapter body 12 and tip cap 20, such as by being removably connected to the exterior of the tip cap 20. Such removable connection may be accomplished by a frangible connector or attachment 49. Therefore, one structural embodiment of the retainer structure 42 may comprise a retaining ring, having an annular configuration removably disposed in surrounding relation to the exterior of both the tip cap 20 and the adaptor body 12.

When access to the internal contents of the syringe 100 is contemplated, subsequent to the fixed connection of the discharge port 102 of the syringe 100 to the adapter body 12, the sleeve 40 may be removed from the adapter body 12 and attached tip cap 20. Such removal is accomplished by exerting a pulling force on the sleeve 40, as represented schematically by directional arrow 50 shown in FIG. 3. Such pulling force 50 will dispose the retainer structure 42 in interruptive engagement with the internal stepped portion 48 of the sleeve 40. Due to the frangible connection 49, the retainer structure 42 will be disconnected from the exterior of the tip cap 20. Allowing removal of the sleeve 40 concurrent to passage of the adapter body 12 and connected tip cap 20 through the open end 46 of the sleeve 40.

As such, removal of the sleeve 40 and detachment of the retainer structure 42 from the tip cap 20, will provide a clear evidence of attempted access to the contents of the syringe 100 and/or tampering. Moreover, due to the transverse dimension of the retainer structure 42 being greater than that of the sleeve portion 41 and access opening 18, the retainer structure 42 may be captured within the sleeve 40, after its detachment from the tip cap 20.

As set forth above, different embodiments of the adaptor closure 10 and 10' include structural modifications which facilitate the connection thereof respectively to a male or female standardized connector, including ISO series 80369-3 ENFit® connector (not shown).

Therefore, and with primary reference now to FIGS. 4-6, the closure 10' comprises an adapter body 12' including an inlet segment or inlet port 14' and an outlet segment or outlet port 16'. The inlet and outlet ports 14' and 16' are disposed in fluid communication with one another by an interconnecting opening 17. The adapter body 12' also includes an access opening 18 through which a discharge port 102 of the syringe 100 passes. The aforementioned "push-on" connection of the discharge port 102 of the syringe 100 forces the discharge port 102 through the inlet port 14' and into a fluid tight engagement on the interior of the outlet port 16', as represented in FIG. 5. As such, the interior of the inlet port 14' has a substantially open, at least partially female configuration which allows passage of the discharge port 102 there-through. Further, while the outlet port 16' has an exterior mail configuration so as to be connected to a female standardized connector, the interior of the outlet port 16' has a female configuration so as to receive the discharge port 102 therein in a fluid sealing engagement therewith. Accordingly, the closure 10' is structured to facilitate connection of the syringe 100 and discharge port 102 to a female standardized connector, including a female ENFit® connector (not shown).

Further, and still referring to FIGS. 4-6, the closure 10' preferably includes a tip cap 20' that is dimensioned, configured and appropriately structured to establish a fluid sealing engagement with the outlet segment or outlet port 16' of the adapter body 12'. As such, the tip cap 20' includes a flow restrictor 22' at least partially defined by the interior of the outlet port 16' and includes a closed female configuration, as represented in FIG. 4 and as set forth above. As such, the closed female flow restrictor 22' is disposed in fluid sealing engagement with the flow restrictor 102 and prevents escape from the contents of the syringe 100, while the tip cap 20' is connected to the adapter body 12 by.

As also represented in FIGS. 4 and 5, the adapter body 12' includes one or more outwardly extending ribs or "threads" 24, structured to establish a rotational threaded engagement with thread structure 26, formed on the tip cap 20'. This rotational threaded engagement of the tip cap 20' with the outlet segment or outlet port 16' of the adapter body 12' maintains the disposition of the female flow restrictor 22' of the tip cap 20' in the aforementioned fluid sealing engagement with the discharge port 102 of the syringe 100.

Structural features of the closure 10' which further facilitate both the rotational, threaded attachment and detachment of the tip cap 20' from the adapter body 12' and corresponding inlet segment or port 16' include a movement restrictor 30. Similar to the embodiment of FIGS. 2 and 3, the movement restrictor 30 is preferably disposed within the adapter body 12' between and adjacent the access opening 18 and inlet port or inlet segment 14'. The movement restrictor 30 may include the flexible material construction and annular configuration, described previously, and may also include a substantially open central interior. In addition, the movement restrictor 30 comprises a plurality of outwardly protruding, spaced apart teeth 32 as shown in FIG. 4. One end of the adapter body 12' associated with the access opening 18, includes the interior surface recess 34 disposed, dimensioned and configured to fixedly retain the movement restrictor 30 therein, preferably by a "snap-fit" insertion. The disposition as well as the structural and operative features of the movement restrictor 30 will be substantially equivalent to the movement restrictor 30 as described in detail with reference to the embodiment of FIGS. 2 and 3. As such, the movement restrictor 30 will be "fixedly" attached within the adapter body 12' in the intended operative position, as set forth above and represented in the Figures.

Therefore, when the movement restrictor 30 is in the intended operative position, the discharge port 102 of the syringe 100 will enter the adapter body 12' for interconnection with the inlet segment or port 14' through the access opening 18 and through the open interior of the movement restrictor 30. The discharge port 102 of the syringe 100 will then be fixedly connected to the adapter body 12' as represented in FIG. 4. As set forth above, the "fixed connection" of the discharge port 102, relative to the inlet segment port 14', restricts and substantially prevents removal or rotation of the discharge port 102 and syringe 100 relative to the adapter body 12. Such a fixed connection is accomplished, at least in part, by the aforementioned flexible characteristics of the movement restrictor 30 in cooperation with the gripping engagement of the plurality of fingers 32 and interior surface portions of the movement restrictor 30 with the outer surface of the discharge port 102.

In order to establish and assure a fluid tight connection with the discharge port 104 and the interior of the outlet port 16', the tip cap 20' preferably also includes a one-way drive structure generally indicated at 60. In more specific terms, the one-way drive structure 60 comprises cooperatively disposed one way drive component 62 and 64 respectively formed on the interior end of the tip cap 20' and on the interior surface of the closed end 44'. As represented in FIG. 5, when the "push-on" force is exerted on the syringe 100, the adapter body 12' and the connected tip cap 20' will be forced inwardly towards the interior surface of the closed end 44' of the sleeve 40'. This will result in a mating engagement of the one way drive components 62 and 64. When the one way drive components 62 and 64 are so engaged, the one-way drive structure 60 is operable to at least temporarily lock the adapter body 12' and connected tip cap 20' into the interior of the sleeve 40' and prevent relative rotation between the sleeve 40' and the connected adaptor body 12' and tip cap 20'. As a result, an external preferably clockwise twisting or turning of the syringe 100, when the discharge port 102 is within the outlet port 16', will cause a tightening therebetween, which in turn assures a fluid tight connection. It is also to be noted that the drive structure 60 including both drive component 62 and 64 can be incorporated in the embodiment of FIGS. 2 and 3 and can be in the form of a one way ramp and cliff drive assembly.

It is further emphasized that the discharge port 102 is sufficiently restricted against rotation relative to the adapter body, due to its engagement with the movement restrictor 30, to allow the tip cap 20' to be rotationally unthreaded and subsequently reattached, by a rotational threaded connection, when sleeve 40 has been removed from the adapter body 12'. However, the exertion of a tightening force on the syringe 100 and discharge port 102 can still be accomplished to tighten the fluid sealing connection between the exterior of the discharge port 102 and the flow restrictor 22' and/or interior of the outlet port 16'.

Therefore, restricted removal or rotation of the discharge port 102 relative to the adapter body 12' will allow a rotational, detachment (threaded) of the tip cap 20' from the outlet segment or port 16'. The fixed connection of the discharge port 104 relative to the adapter body 12 will also allow the tip cap 20 to be rotationally (threaded) re-attached in its sealing engagement with the outlet segment or port 16'.

With further reference to FIGS. 4 and 5, the closure 10' preferably also includes tamper evident capabilities defined, at least in part, by a tamper evident assembly including the sleeve 40' and a retainer structure 42'. The sleeve 40' is disposed in surrounding, enclosing relation to both the adapter body 12' and the tip cap 20' and includes a closed end 44' and an oppositely disposed open end 46. The open end 46 is disposed substantially adjacent to and in coaxial alignment with the access opening 18 of the adapter body 12'. This alignment facilitates positioning and push-on connection of the discharge port 102 of the syringe 100 into the aforementioned fluid sealing connection with the outlet segment or outlet port 14', through the access opening 18 and the open central portion of the movement restrictor 30.

Similar to the embodiment of FIGS. 2 and 3, the internal diameter or transverse dimension of the portion 41 of the sleeve 40' is smaller than that of the sleeve portion 41'. As a result, the interior surface portion of the sleeve 40' includes a "stepped" configuration or structure 48'. The stepped interior surface 48' may further define the junction of the smaller dimensioned sleeve portion 41 with the larger dimensioned sleeve portion 41'.

In cooperation therewith, the retainer structure 42' includes a diameter or transverse dimension which is larger than that of the sleeve portion 41 and more closely corresponding to that of the sleeve portion 41'. The retaining member 42' is disposable in interruptive relation with the interior surface stepped portion 48' of the sleeve 40. As with the embodiment of FIGS. 2 and 3, the retainer structure 42 is removably disposed on the exterior of both the adapter body 12' and tip cap 20'. Accordingly, the retainer structure 42' may be connected to the exterior of the tip cap 20' by a frangible connection or attachment 49.

As represented in FIG. 6, when access to the contents of the syringe 100 is contemplated and subsequent to the fixed connection of the discharge port 102 of the syringe 100 to the adapter body 12', the sleeve 40' may be removed from the adapter body 12' and attached tip cap 20'. Such removal is accomplished by exerting a pulling force 50 on the sleeve 40'. Such pulling force 50 will dispose the retainer structure 42' in interruptive engagement with the internal stepped portion 48' of the sleeve 40'. Due to the frangible connection 49, the retainer structure 42' will be disconnected from the exterior of the adapter body 12', allowing removal of the sleeve 40' by passage of the adapter body 12' and connected tip cap 20' through the open end 46 of the sleeve 40.

As with the embodiment of FIGS. 2 and 3, such removal of the sleeve 40' and detachment of the retainer structure 42' from the tip cap 20', and the possible capturing of the retainer structure 42' within the interior of the sleeve 40', will provide a clear evidence of attempted access to the contents of the syringe 100 and/or tampering.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure structured to adapt a syringe for connection to an incompatible standardized connector, said closure comprising:
   an adapter body including an inlet port and an outlet port disposed in fluid communication with one another,
   said inlet port structurally adapted to accommodate a connection of a discharge port of the syringe with said adaptor body,
   said outlet port structurally adapted to accommodate a fluid communicating connection to the standardized connector,
   a movement restrictor connected to said adapter body in movement restricting engagement with the discharge port of the syringe,
   a tip cap removably connected to said adapter body in flow sealing relation to said outlet port, a tamper evident assembly including a sleeve removably disposed in enclosing relation to said adapter body and said tip cap, said sleeve including an open end disposed adjacent an access opening of said adapter body, said tamper evident assembly further including a retainer structure removably disposed exteriorly of said adapter body in retaining relation to said sleeve, said sleeve including an interior surface portion disposed in disconnecting engagement with said retainer structure, concurrent to removal of said adapter body through said open end, and said interior surface comprising a stepped construction defining and inwardly directed flange disposed in at least partially surrounding relation to said tip cap and in engaging relation to said retainer structure.

2. The closure as recited in claim 1 wherein said movement restrictor is disposed in fixedly interconnecting relation between the discharge port of the syringe and the adapter body, concurrent to attachment and detachment of said tip cap relative to said outlet port.

3. The closure as recited in claim 1 wherein said tip cap comprises a flow restrictor connected in flow sealing relation to said outlet port, said flow restrictor at least partially dimensioned and configured to correspond to a portion of the standardized connector.

4. The closure as recited in claim 3 wherein said flow restrictor comprises a male configuration cooperatively dimensioned and configured to a female configuration of said outlet port.

5. The closure as recited in claim 3 wherein said flow restrictor comprises a female configuration cooperatively dimensioned and configured to a male configuration of said outlet port.

6. The closure as recited in claim 1 wherein said movement restrictor is disposed within said adapter body, exteriorly of said inlet port and in rotation restricting engagement with an exterior of the discharge port of the syringe.

7. The closure as recited in claim 6 wherein said adapter body comprises an interior recess cooperatively dimensioned with said movement restrictor to define a locking, snap-fit connection therebetween.

8. The closure as recited in claim 6 wherein said movement restrictor comprises a plurality of teeth at least partially and collectively disposed in movement restricting engagement with an exterior of the discharge port.

9. The closure as recited in claim 6 wherein said movement restrictor comprises a flexible material washer including a plurality of teeth collectively disposed in surrounding, rotation restricting engagement with an exterior of the discharge port of the syringe.

10. The closure as recited in claim 1 wherein said retainer structure is removably connected to an exterior of said tip cap in interruptive relation with said interior surface portion.

* * * * *